United States Patent
Skaberna

(10) Patent No.: US 7,233,646 B2
(45) Date of Patent: Jun. 19, 2007

(54) COMPUTERIZED METHOD FOR GENERATING A SCHEDULE FOR IMPLEMENTING EXAMINATION WITH AN X-RAY APPARATUS

(75) Inventor: Sven Skaberna, Wiesenthau (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 11/216,637

(22) Filed: Aug. 31, 2005

(65) Prior Publication Data

US 2006/0050849 A1 Mar. 9, 2006

(30) Foreign Application Priority Data

Aug. 31, 2004 (DE) ...................... 10 2004 042 485

(51) Int. Cl.
*H05G 1/36* (2006.01)
(52) U.S. Cl. ............................ 378/118; 705/3; 378/162
(58) Field of Classification Search ................ 378/118, 378/162, 165; 705/3
See application file for complete search history.

(56) References Cited

U.S. PATENT DOCUMENTS

| | | | | | |
|---|---|---|---|---|---|
| 4,032,788 A | * | 6/1977 | Stege et al. | ................... | 378/98 |
| 4,811,374 A | * | 3/1989 | Kasa et al. | ................... | 378/96 |
| 5,809,106 A | * | 9/1998 | Kitade et al. | ............... | 378/132 |
| 6,377,657 B1 | * | 4/2002 | Scholz | ....................... | 378/118 |
| 6,542,579 B1 | * | 4/2003 | Takasawa | ................... | 378/165 |
| 2002/0099571 A1 | * | 7/2002 | Waku et al. | ................... | 705/2 |
| 2005/0055246 A1 | * | 3/2005 | Simon | ........................... | 705/2 |

* cited by examiner

*Primary Examiner*—Edward J. Glick
*Assistant Examiner*—Anastasia S. Midkiff
(74) *Attorney, Agent, or Firm*—Schiff Hardin LLP

(57) ABSTRACT

In a method and a computer for generating a schedule for the implementation of examinations with an x-ray apparatus, in particular an x-ray computed tomography apparatus, a particularly exact schedule is generated by calculating an occupation duration for each patient using a load calculator that is present in the x-ray apparatus and to generate a schedule based on the calculated occupation duration, also taking into account a wait time for each examination.

26 Claims, 2 Drawing Sheets

| Appointment | Name | Examination protocol | Occupation duration | Wait time |
|---|---|---|---|---|
| 08:00 | Meier | A2 | 25 Min. | 05 Min. |
| 08:25 | Lutz | C4 | 45 Min. | 12 Min. |
| 09:00 | Schmitt | A2 | 28 Min. | 08 Min. |
| 09:28 | Hase | C1 | 53 Min. | 14 Min. |
| 10:21 | Weiler | A2 | 28 Min. | 08 Min. |
| 10:49 | Friedrich | A2 | 27 Min. | 07 Min. |
| 11:16 | Bauer | D1 | 36 Min. | 09 Min. |

FIG 2

| Appointment | Name | Examination protocol | Occupation duration | Wait time |
|---|---|---|---|---|
| 08:00 | Meier | A2 | 25 Min. | 05 Min. |
| 08:25 | Lutz | C4 | 45 Min. | 12 Min. |
| 09:00 | Schmitt | A2 | 28 Min. | 08 Min. |
| 09:28 | Hase | C1 | 53 Min. | 14 Min. |
| 10:21 | Weiler | A2 | 28 Min. | 08 Min. |
| 10:49 | Friedrich | A2 | 27 Min. | 07 Min. |
| 11:16 | Bauer | D1 | 36 Min. | 09 Min. |
| ⋮ | ⋮ | ⋮ | ⋮ | ⋮ |

FIG 3

| Time | | Name / Examination protocol | Wait time |
|---|---|---|---|
| 08:00 | ▨ | Meier / A2 | 05 Min. |
| 08:30 | ▨ | Lutz / C4 | 12 Min. |
| 09:00 | ▨ | Schmitt / A2 | 08 Min. |
| 09:30 | ▨ | Hase / C1 | 14 Min. |
| 10:00 | ▨ | Weiler / A2 | 08 Min. |
| 10:30 | ▨ | Friedrich / A2 | 07 Min. |
| 11:00 | ▨ | Bauer / D1 | 09 Min. |
| 11:30 | ▨ | ⋅ | ⋅ |
| 12:00 | ⋮ | ⋅ | ⋅ |
| 12:30 | | ⋅ | ⋅ |

# COMPUTERIZED METHOD FOR GENERATING A SCHEDULE FOR IMPLEMENTING EXAMINATION WITH AN X-RAY APPARATUS

BACKGROUND OF THE INVENTION

1. Field of the Invention

The invention concerns a method for generation of a schedule for the implementation of examinations with an x-ray apparatus, in particular an x-ray computed tomography apparatus. The invention also concerns the use of a load calculator as well as a computer for execution of a program for implementation of the method.

2. Description of the Prior Art

According to the prior art, dates for implementation of examinations using an x-ray apparatus are assigned by medical auxiliary personnel, for example using a computer-aided schedule planner. The name of the patient, the examination to be implemented as well as an anticipated occupation time of the apparatus is entered in the procedure for assignment of a date. The estimation of the occupation time encompasses an estimation of the actual examination duration and a wait time. The wait time is necessary for cooling of the x-ray tube. During the wait time, operation of the x-ray apparatus is not possible. The length of the wait time depends on a number of parameters, for example the selected examination time, the examination duration as well as the number of previously-implemented examinations, and the like. As a consequence, the occupation duration can be different for the same examination, conducted at different times. A precise estimation of the occupation duration for a given examination requires experience. Occupation durations are particularly difficult to precisely estimate for inexperienced personnel. Errors in the estimation of the occupation durations accumulate over the day and either lead to an inadequate utilization of the x-ray apparatus or to bothersome wait times for the patient.

According to the prior art, DE 198 11 041 A1 a load calculator is disclosed that is a component of the x-ray apparatus. The temperature distribution of the anode of the x-ray tube is continuously calculated. After the end of a measurement, a wait time is determined on the basis of the calculated temperature distribution, and operation of the x-ray apparatus is blocked for the duration of the wait time to prevent a thermal overload of the x-ray tube. In this known method, the wait time for the purpose of a sufficient cooling of the x-ray tube is calculated exclusively on the basis of the power consumption up to the time of the examination under consideration.

SUMMARY OF THE INVENTION

An object of the present invention is to overcome the disadvantages according to the prior art in a precise method for generation of a schedule for the implementation of examinations with an x-ray apparatus, making use of a load calculator. A computer for execution of a program for implementation of the method also is encompassed by the invention.

The above object is achieved in accordance with the invention by a method for generation of a schedule for the implementation of examinations on an x-ray apparatus, in particular an x-ray computed tomography apparatus, wherein a data set containing at least the name of the patient and the examination protocol to be used for the examination, is provided, and wherein on the basis of the examination protocol, an occupation duration of the x-ray apparatus necessary for the examination is calculated using a load calculator that calculates the temperature of the anode of the x-ray apparatus, and wherein the occupation duration calculated for the patient is displayed.

The inventive method enables the generation of an exact schedule for the implementation of examinations with an x-ray apparatus. It is no longer necessary to estimate the occupation duration according to experiential values. The occupation duration is determined by means of the load calculator using the examination protocol.

As used herein an "examination protocol", means a conventional examination protocol for implementation of x-ray examinations. The examination protocol in particular contains specific parameters with which a predetermined operating mode (such as the power consumption of the x-ray tube) is set. As used herein, "load calculator," means a data processing device or a computer that is a component of the x-ray apparatus. This computer can be linked to a computer network. A program for calculation of a temperature of the anode of the x-ray tube is provided on this computer. The temperature distribution determined with the load calculator can be used for calculation of the wait times that are necessary after the implementation of an examination for cooling of the x-ray tube. Such a load calculator is known according to the prior art, for example from DE 198 11 041 A1 (the disclosure of which is incorporated herein by reference).

The occupation duration can include the examination duration and the wait time necessary for cooling of the anode, and the examination duration and the wait time can be displayed separately. A minimum wait time that must be adhered to before the execution of a further examination protocol can be calculated on the basis of the examination protocol predetermined for a patient. The examination duration can be manually predetermined by the personnel. A manual specification is particularly well suited for standardized examinations in which the examination durations are essentially constant and can simply be estimated using a standard examination duration. It is also possible to store a predetermined examination duration with regard to a selected examination protocol. In this case, the examination duration does not have to be separately, manually entered by the personnel. Selection of a specific examination protocol from a predetermined table is sufficient. The examination duration can also be calculated using a simulation. For this purpose, an examination protocol to be executed in an examination can be simulated. The total duration can be determined on the basis of the boundary condition that a predetermined upper limit of the temperature of the anode will not be exceeded. Given transgression of the upper limit, additional wait times can be provided at suitable points for the examination protocol.

A simulation can be used with arbitrary examination protocols, and in particular given non-standard or newly-developed examination protocols. For newly-developed examination protocols, it can be that no sufficient experiential values may exist for a precise estimation of the examination duration or wait duration.

The occupation duration is appropriately calculated by the load calculator from the power consumption of the x-ray apparatus dependent on preceding examinations. The power consumption as a result of one or more preceding examinations can significantly influence the temperature of the anode at the beginning of a further examination. As a consequence of heating of the housing surrounding the anode or the coolant used to cool the anode, the heat radiation or the heat dissipation may be reduced. That can lead to a faster heating and consequently to longer wait times. In order to account for such influences in the calculation of the examination duration or the occupation duration, a simulation is used. For example, a temperature curve of the anode that is specific for individual, successive examination protocols can be calculated with the load calculator. The occupation or examination duration can be calculated with particular precision using the temperature curve. In the simulation, it is also possible to determine an optimized sequence of the examinations to formulate a list of predetermined examination protocols. The optimization can ensue, for example, under the boundary condition of a particular small average, maximal anode temperature, a minimum overall duration of the examinations, or the like. As a boundary condition it can also be predetermined that one or more selected examinations from a list of examinations will be executed at a fixed, predetermined point in time and that the wait times between the examinations of the list and/or their overall occupation duration are/is minimal. The inventive calculation of the occupation duration enables a particularly exact calculation of the occupation duration dependent on the preceding power consumption.

According to a further embodiment, a table reproducing an occupation sequence is created that contains the names of the patients and the occupation durations and/or wait times determined therefor.

Using the predetermined examination protocol as well as the predetermined examination duration, the temperature to be expected and an occupation duration and/or wait time necessary for cooling can be calculated with a conventional load calculator. That can be implemented for each of the data sets in the predetermined occupation sequence. The proposed simulation calculation as a result leads to an occupation duration for each of the data sets. Starting from the beginning or the end of a calculated occupation duration, the personnel can notify the patient of an exact appointment. The appointment is, for example, selected 10 minutes before the beginning of the occupation duration so that the patient can still be prepared beforehand for the examination.

In a further embodiment, the occupation duration is selected so that the sum of the wait times is minimal. For this purpose, the occupation sequence, for example, can be manually changed by the personnel. An optimal occupation sequence also can be determined using a simulation. A temperature distribution calculated by the load calculator for a predetermined examination sequence can be used for calculation of the examination durations, wait times and the like. For example, the succession of the examinations can be permutated so that the wait times are minimal. Apart from this, any other optimization technique can be used for minimization of the wait times. The sum of the wait times can respectively be calculated and displayed to the user to monitor whether an improved occupation sequence has been achieved with regard to the sum of the wait times.

According to a further embodiment, the occupation sequence is selected so that the occupation duration at the end of the table exhibits a maximum wait time. This means that the last appointment made on an examination day is used, for example, for an examination in which a particularly high power consumption (and with this a particularly long wait time) is not to be expected. In this case, the long wait time that would occur following such an examination does not contribute to preventing of the operation of the x-ray apparatus at capacity, since for this examination date no further occupation of the x-ray apparatus occurs afterwards.

The data concerning the patient preferably are extracted from an electronic databank. This can be a databank of a patient administration program used in a hospital. Errors in data input are prevented by the transfer of the data from such a databank. An examination protocol provided for the patient also can be transferred with the data. The examination protocol, for example, can have been provided earlier by a treating physician.

The examination protocols, however, also can be selected from a further electronically stored table of predetermined examination protocols. An examination duration can be associated with each of the examination protocols.

According to a further embodiment of the method, given a change of the occupation sequence, the occupation durations are automatically recalculated and displayed. A change of the occupation sequence can result, for example, due to the cancellation of an appointment. In this case, the schedule can be recalculated. The patients can be notified of changed appointments that result.

According to a further embodiment of the method, the occupation sequence is automatically changed after the calculation of the occupation durations so that the sum of the occupation durations is minimal. Such a calculation can ensue using conventional algorithms. Such algorithms aim for a minimization of the sum of the wait times. They enable an optimal utilization of the x-ray apparatus.

Also in accordance with the invention, a load calculator is used for calculation of the temperature of an anode of an x-ray apparatus to create a schedule for the implementation of examinations. The temperature distribution of the anode that is detected by a load calculator (known, for example, from DE 198 11 041 A1) can be used for simulation of the occupation durations, the examination times as well as the wait times. The simulation can form the basis of predetermined examination protocols, for example in the form of a list. In the load calculator a function can be provided by means of which the data sets necessary for calculation (if applicable corresponding to the occupation sequence) can be transferred or adopted. The data sets preferably are automatically transferred from a databank such as, for example, a clinical information system or a patient databank of a hospital, etc. A start time can be taken into account the calculation of the occupation durations. The start time is the point in time of the examination acquisition on an examination date. The start time can be freely selected. The beginning of the occupation durations as well as the length of the wait time can additionally be output as a result. The aforementioned functions can be combined into a program that is provided on a computer networked with the load calculator. The program also can perform the auxiliary function of serving as a conventional appointment-planning program, i.e. it can be integrated into a conventional appointment-planning program.

According to a further embodiment of the invention, a computer is provided for execution of a program for implementation of a method for generation of a schedule for the implementation of examinations on an x-ray apparatus, that performs the steps of providing a data set containing at least the name of the patient and the examination protocol to be used for the examination, calculating on the basis of the examination protocol, an occupation duration of the x-ray apparatus necessary for the examination using a load calculator to calculate the temperature of the anode of the x-ray apparatus, and displaying the occupation duration calculated for the patient.

The generation of an exact schedule for the implementation of examinations with an x-ray apparatus is possible with the inventive computer. In particular it is no longer necessary to estimate the occupation duration using experiential values. The computer can be the load calculator itself, a computer that can access on a network and so as to become connected with the load calculator or a computer provided for control of the x-ray apparatus.

DESCRIPTION OF THE DRAWINGS

FIG. 2 shows an example of an input and result table in accordance with the inventive method.

FIG. 3 shows an example of a schedule generated by the inventive method.

DESCRIPTION OF THE PREFERRED EMBODIMENTS

Figure 1:
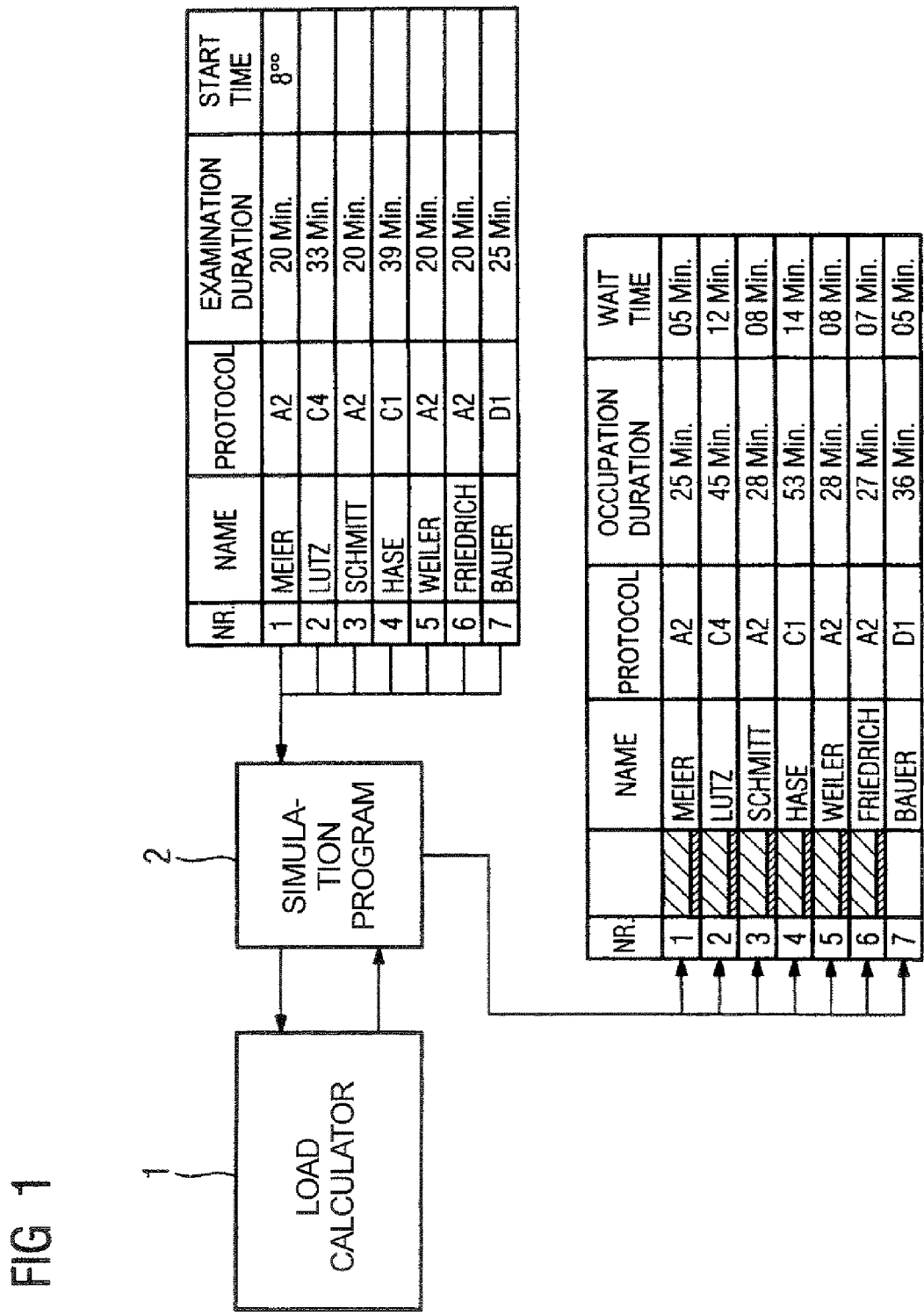
FIG. 1 schematically illustrates the basic steps of the inventive method, as well as a computer arrangement in accordance with the invention for implementing a method

In FIG. 1 a load calculator 1 is shown that is a component of an x-ray apparatus, for example of an x-ray computed tomography apparatus. The temperature of the anode is calculated with the load calculator 1 in a conventional manner based on predetermined power requirements. A wait time during which operation of the x-ray apparatus is blocked to prevent damage to the anode is calculated dependent on the temperature values calculated by the load calculator 1. During the wait time the anode cools to a temperature that will allow the power requirement for the next examination to be satisfied.

A simulation program 2 is provided on a computer that, for example, networked with the load calculator so the computer can access the capabilities of the known load calculator 1. Stored examination protocols as well as at least one start time specified for the first stored examination protocol are taken (read) in succession from a table according to an occupation sequence, and a wait time resulting therefrom is then calculated using the load computer 1. The calculated wait times are written in a further table according to the occupation sequence.

A fixed, predetermined examination device can be stored with regard to a particular examination protocol. Alternatively, entries into the examination device can be made manually by an operator. With the simulation program 2 it is possible to add the examination duration and the respectively determined wait time for each of the data sets of the occupation sequence. The sum yields an occupation duration. For example, the end of an occupation duration can be used as the appointment time for the next following examination. Starting from the end of the occupation duration, however, it is also possible to calculate a somewhat earlier appointment that enables preparation of the patient. The calculation of the appointment can ensue according to predetermined parameters. For example, an appointment to be assigned to a patient can be 10 minutes before the end of the occupation duration for the previous examination.

As can be seen from FIG. 1, the examination duration and the wait time can be separately (for example graphically) displayed in the result table.

FIG. 2 shows an exemplary embodiment of such a result table. The essential data determined with the load computer 1 and the simulation program 2 are reproduced in this result table, namely the date, the name, the examination protocol, the occupation duration and the wait time contained in the occupation duration.

As can be seen from FIG. 3, the result also can be prepared as a type of schedule in which the examination duration and the wait times are graphically shown along a time axis.

In an embodiment, the occupation sequence can be selected by the simulation program 2 so that the sum of the wait times is minimized. According to a further option of the simulation program 2, it is possible to place an occupation duration that exhibits a maximum wait time at the end of the occupation sequence. Such a wait time then does not lead to a reduced utilization of the x-ray apparatus because a further occupation does not occur thereafter, so the long wait time consequently plays no role.

The examination protocols A2, C1, C4, D1 shown in FIGS. 1 through 3 can be selected by the user from a predetermined table of examination protocols. Predetermined examination durations can be respectively associated with the examination protocols, or the examination duration can be manually changed.

According to a further embodiment of the simulation program 2, the user is permitted to change the occupation sequence, for example due to the cancellation of an appointment by a patient. In this case, the occupation durations and the wait times can be automatically recalculated. Furthermore, with the simulation program 2 it is also possible to automatically calculate an occupation sequence such that the sum of the occupation durations is minimized. A particularly high utilization of the x-ray apparatus is thereby achieved.

Although modifications and changes may be suggested by those skilled in the art, it is the intention of the inventor to embody within the patent warranted hereon all changes and modifications as reasonably and properly come within the scope of his contribution to the art.

I claim:

1. A computerized method for generating a schedule for implementing examinations with an x-ray apparatus, said x-ray apparatus having an anode and a load calculator that calculates a temperature of the anode, said method comprising the steps of:

providing a data set to a computer, said data set containing respective names of a plurality of patients and respective examination protocols for examining the respective patients with said x-ray apparatus;

in said computer, calculating an occupation duration of the x-ray apparatus necessary for each of said examinations that includes an examination duration and a wait time necessary for cooling of the diode, using said load calculator to calculate the temperature of the anode of the x-ray apparatus, calculating an occupation sequence so that a sum of said wait times is minimized; and from said computer, displaying the occupation duration calculated for the patient displaying a table containing an occupation sequence wherein all of said occupation durations are ordered in said sequence and containing, for each occupation duration, the name of the patient associated therewith and the wait time associated therewith.

2. A computerized method as claimed in claim 1 comprising, displaying said examination duration for each of said patients, and said wait time separately in said table.

3. A computerized method as claimed in claim 1 comprising using said load calculator to calculate a power consumption of said x-ray apparatus dependent on at least one examination using said x-ray apparatus preceding said examination of each patient.

4. A computerized method for generating a schedule for implementing examinations with an x-ray apparatus, said x-ray apparatus having an anode and a load calculator that calculates a temperate of the anode, said method comprising the steps of:

providing a data set to a computer, said data set containing respective names of a plurality of patients and respective examination protocols for examining the respective patients with said x-ray apparatus;

in said computer, calculating an occupation duration of the x-ray apparatus necessary for each of said examinations that includes an examination duration and a wait time necessary for cooling of the diode, using said load calculator to calculate the temperature of the anode of the x-ray apparatus;

in said computer, ordering said occupation durations in an occupation sequence that places an occupation duration at an end of said occupation sequence that has a maximum wait time associated therein; and from said computer, displaying the occupation duration calculated for the patient displaying a table containing an occupation sequence wherein all of said occupation durations are ordered in said sequence and containing, for each occupation duration, the name of the patient associated therewith and the wait time associated therewith.

5. A method as claimed in claim 1 comprising, in said computer after calculation of said occupation sequence, allowing manual modification of said occupation sequence and comprising, after a manual modification of said occupation sequence, automatically recalculating said occupation sequence in said computer and displaying the recalculated occupation sequence.

6. A computerized method for generating a schedule for implementing examinations in an x-ray apparatus, said x-ray apparatus having an anode and load calculator that calculates a temperature of the anode, said method comprising the steps of:

providing a data set to a computer, said data set containing respective names of a plurality of patients and respective examination protocols for examining the respective patients with said x-ray apparatus;

in said computer, calculating an occupation duration of the x-ray apparatus necessary for each of said examinations that includes an examination duration and a wait time necessary for cooling of the diode, using said load calculator to calculate the temperature of the anode of the x-ray apparatus;

calculating an occupation duration for each of said patients and each of said examinations using said load calculator;

from said computer, displaying the occupation duration calculated for the patient displaying a table containing an occupation sequence wherein all of said occupation durations are ordered in said sequence and containing, for each occupation duration, the name of the patient associated therewith and the wait time associated therewith;

in said computer, after calculation of said occupation sequence, allowing manual modification of said occupation sequence, automatically recalculating said occupation sequence to minimize a sum of said occupation durations in the recalculated occupation sequence, and displaying the recalculated occupation sequence.

7. A method as claimed in claim 1 comprising providing said data set to said computer by extracting said data set from among a plurality of data sets electronically stored in a data bank.

8. A method as claimed in claim 1 comprising selecting said examination protocol from among a plurality of examination protocols electronically stored in a table.

9. A computer having a computer program loaded therein, said computer program comprising electronically readable data stored on a storage medium for causing said computer to generate a schedule for implementing examinations with an x-ray apparatus, said x-ray apparatus comprising an anode and having a load calculator that calculates a temperature of the anode, said computer program causing said computer to:

receive a data set containing a name of a patient and an examination protocol for conducting an examination of the patient with the x-ray apparatus, said data set comprising a plurality of names of respective patients and a plurality of examination protocols respectively for examining said patients with said x-ray apparatus;

calculate, dependent on said examination protocol, an occupation duration of the x-ray apparatus necessary for the examination of each of said patients that includes a wait time necessary for cooling of the anode, using said load calculator to calculate the temperature of the anode to calculate said occupation sequence by minimizing a sum of said wait times; and to generate and visually display a table containing said occupation sequence. comprised of an ordered sequence of the respective occupation durations, containing, for each occupation duration, the patient associated therewith and the wait time associated therewith.

10. A computer as claimed in claim 9, wherein said computer program causes said computer, for each of said patients, to display said examination duration and said wait time separately in the display of said occupation duration.

11. A computer as claimed in claim 9 wherein said computer program causes said computer to calculate said occupation duration using the load calculator based on a power consumption of said x-ray apparatus dependent on an examination using said x-ray apparatus preceding said examination of said patient.

12. A computer having a computer program loaded therein, said computer program comprising electronically readable data stored on a storage medium for causing said computer to generate a schedule for implementing examinations with an x-ray apparatus, said x-ray apparatus comprising an anode and having a load calculator that calculates a temperature of the anode, said computer program causing said computer to:

receive a data set containing a name of a patient and an examination protocol for conducting an examination of the patient with the x-ray apparatus, said data set comprising a plurality of names of respective patients and a plurality of examination protocols respectively for examining said patients with said x-ray apparatus;

calculate, dependent on said examination protocol, an occupation duration of the x-ray apparatus necessary for the examination of each of said patients that includes a wait time necessary for cooling of the anode, using said load calculator to calculate the temperature of the anode and to calculate an occupation sequence that places an occupation duration at an end of said occupation sequence that has a maximum wait; and to generate and visually display a table containing said occupation sequence, comprised of an ordered sequence of the respective occupation durations, containing, for each occupation duration, the patient associated therewith and the wait time associated therewith.

13. A computer as claimed in claim 9 wherein said computer program allows a manual modification of said occupation sequence and causes said computer, after a manual modification of said occupation sequence, to automatically recalculate a recalculated occupation duration and to display said recalculated occupation duration.

14. A computer having a computer program loaded therein, said computer program comprising electronically readable data stored on a storage medium for causing said computer to generate a schedule for implementing examinations with an x-ray apparatus, said x-ray apparatus comprising an anode and having a load calculator that calculates a temperature of the anode, said computer program causing said computer to:
  receive a data set containing a name of a patient and an examination protocol for conducting an examination of the patient with the x-ray apparatus. said data set comprising a plurality of names of respective patients and a plurality of examination protocols respectively for examining said patients with said x-ray apparatus;
  calculate, dependent on said examination protocol, an occupation duration of the x-ray apparatus necessary for the examination of each of said patients that includes a wait time necessary for cooling of the anode, using said load calculator to calculate the temperature of the anode;
  to generate and visually display a table containing said occupation sequence, comprised of an ordered sequence of the respective occupation durations, containing, for each occupation duration, the patient associated therewith and the wait time associated therewith; and
  to allow a manual modification of said occupation sequence and, after a manual modification of said occupation sequence, to automatically calculate a recalculated occupation sequence by minimizing a sum of the occupation durations, and to display said recalculated occupation duration.

15. A computer as claimed in claim 9 comprising a data bank in communication with said computer containing said data set, and wherein said computer electronically access said data bank to receive said data set.

16. A computer as claimed in claim 9 comprising a memory containing an electronically stored table comprising a plurality of examination protocols, said memory being accessible by said computer and said computer accessing said memory to select an examination protocol from said table for said patient.

17. A computerized method as claimed in claim 4 comprising using said load calculator to calculate a power consumption of said x-ray apparatus dependent on at least one examination using said x-ray apparatus preceding said examination of each patient.

18. A computerized method as claimed in claim 6 comprising using said load calculator to calculate a power consumption of said x-ray apparatus dependent on at least one examination using said x-ray apparatus preceding said examination of each patient.

19. A method as claimed in claim 4 comprising providing said data set to said computer by extracting said data set from among a plurality of data sets electronically stored in a data bank.

20. A method as claimed in claim 6 comprising providing said data set to said computer by extracting said data set from among a plurality of data sets electronically stored in a data bank.

21. A method as claimed in claim 4 comprising selecting said examination protocol from among a plurality of examination protocols electronically stored in a table.

22. A method as claimed in claim 6 comprising selecting said examination protocol from among a plurality of examination protocols electronically stored in a table.

23. A computer as claimed in claim 12 comprising a data bank in communication with said computer containing said data set, and wherein said computer electronically access said data bank to receive said data set.

24. A computer as claimed in claim 14 comprising a data bank in communication with said computer containing said data set, and wherein said computer electronically access said data bank to receive said data set.

25. A computer as claimed in claim 12 comprising a memory containing an electronically stored table comprising a plurality of examination protocols, said memory being accessible by said computer and said computer accessing said memory to select an examination protocol from said table for said patient.

26. A computer as claimed in claim 14 comprising a memory containing an electronically stored table comprising a plurality of examination protocols, said memory being accessible by said computer and said computer accessing said memory to select an examination protocol from said table for said patient.

* * * * *